US012565523B2

(12) United States Patent
List et al.

(10) Patent No.: US 12,565,523 B2
(45) Date of Patent: Mar. 3, 2026

(54) STRUCTURE-GUIDED ENGINEERING OF PEPTIDE-BASED NLRP3 INFLAMMASOME INHIBITORS FOR MYELODYSPLASTIC SYNDROMES (MDS)

(71) Applicant: H. LEE MOFFITT CANCER CENTER AND RESEARCH INSTITUTE, INC., Tampa, FL (US)

(72) Inventors: Alan List, Tampa, FL (US); Haitao Ji, Tampa, FL (US); Vincent Luca, Tampa, FL (US)

(73) Assignee: H. LEE MOFFITT CANCER CENTER AND RESEARCH INSTITUTE, INC., Tampa, FL (US)

( * ) Notice: Subject to any disclaimer, the term of this patent is extended or adjusted under 35 U.S.C. 154(b) by 1006 days.

(21) Appl. No.: 17/608,021

(22) PCT Filed: May 1, 2020

(86) PCT No.: PCT/US2020/030945
§ 371 (c)(1),
(2) Date: Nov. 1, 2021

(87) PCT Pub. No.: WO2020/223595
PCT Pub. Date: Nov. 5, 2020

(65) Prior Publication Data
US 2022/0324927 A1     Oct. 13, 2022

Related U.S. Application Data

(60) Provisional application No. 62/841,826, filed on May 1, 2019.

(51) Int. Cl.
*C07K 14/47* (2006.01)
*A61P 35/02* (2006.01)
*C12N 15/10* (2006.01)

(52) U.S. Cl.
CPC .......... *C07K 14/4703* (2013.01); *A61P 35/02* (2018.01); *C12N 15/102* (2013.01)

(58) Field of Classification Search
CPC . A61P 31/04; C07K 2317/76; C07K 2317/24; C07K 2317/73; C07K 14/4703; C07K 16/32

USPC ........................................................ 435/69.1
See application file for complete search history.

(56) References Cited

U.S. PATENT DOCUMENTS

2016/0354437 A1     12/2016     Stehlik

FOREIGN PATENT DOCUMENTS

WO     2017129897 A1     8/2017
WO     2017184746 A1     10/2017

OTHER PUBLICATIONS

International Search Report and Written Opinion in PCT/US2020/030945. Mailed Sep. 25, 2020. 14 pages.
Lu et al. Unified Polymerization Mechanism for the Assembly of ASC-depenedent Inflammasomes, Mar. 13, 2014.
Perera et al. MCC950, a specific small molecule inhibitor of NLRP3 inflammasome attenuates colonic infammation in spontaneous colitis mice. Jun. 5, 2018.
Liepinsh, E. et al. The death-domain fold of the ASC PYRIN domain, presenting a basis for PYRIN/PYRIN recognition. J Mol Biol. 332:1155-1163(2003).
Lu, Al. & Wu, H. Structural mechanisms of inflammasome assembly. FEBS Journal. 282(3):435-444(2014).
Mangan, M.S. et al. Targeting the NLRP3 inflammasome in inflammatory diseases. Nature Reviews Drug Discovery. 17(8):588-606(2018).
Oroz, J. et al. ASC Pyrin Domain Self-associates and Binds NLRP3 Protein Using Equivalent Binding Interfaces. J Biol Chem. 291:19487-19501(2016).

*Primary Examiner* — Tekchand Saidha
*Assistant Examiner* — Mohammad Y Meah
(74) *Attorney, Agent, or Firm* — Meunier Carlin & Curfman LLC

(57)          ABSTRACT

Disclosed are compositions and methods for engineered peptide inhibitors of NLRP3 infiammasome and methods of their use in the treatment of Myelodysplastic Syndromes. In one aspect, disclosed herein are engineered inhibitors of NACHT, LRR and PYD domains-containing protein 3 (NLRP3) inflammasome comprising a Helix 2 of POP1 comprising one or more substitutions at residues 18, 21, 22, 25, 26, 28, 29, and/or 30 of POP1 as set forth in SEQ ID NO:1.

9 Claims, 5 Drawing Sheets

Figure 1:
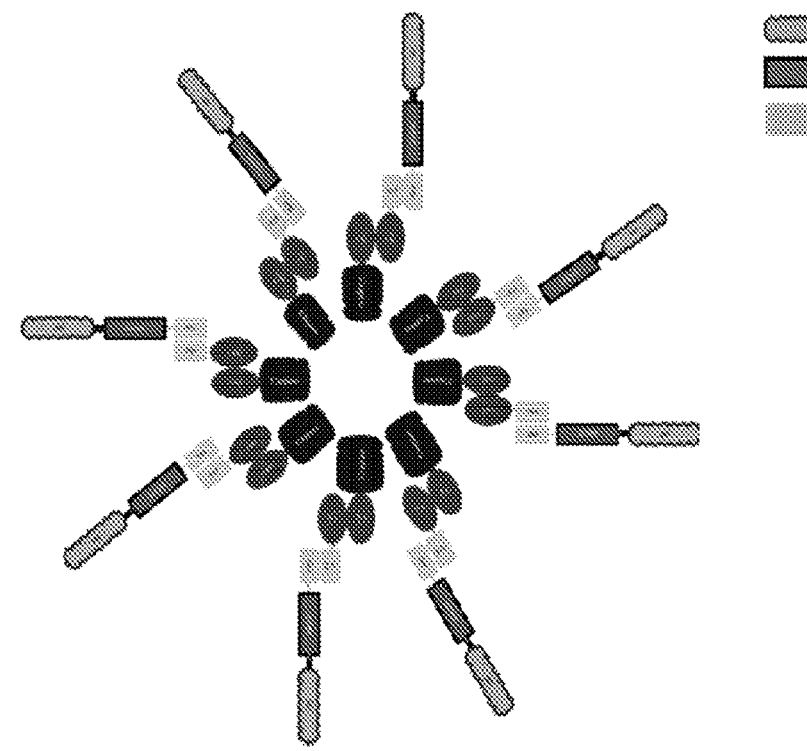

Specification includes a Sequence Listing.

LRR
NACHT
PYD

NLRP3$^{PYD}$      ASC$^{PYD}$

MBP-NLRP3PYD construct

Rigid helical linker:
reduces interdomain flexibility

Maltose Binding Protein (MBP):
Improves solubility, creates crystal contacts

NLRP3PYD

15   LTP⬛⬛ELK⬛FK⬛⬛L⬛⬛PLREG   35

Reduced     Non-reduced

Optimized: pH 7.0-7.7,
PEG 20-28%, Glycerol
5% or 0%

Additive Screen
Optimization 0.19M Calcium Chloride,
0.095M HEPES pH 7.50,
26.6% PEG 400, 5% (v/v)
glycerol 0.2M Calcium Chloride,
0.1M HEPES pH 7.0,
24% PEG 400, 5% (v/v)
glycerol 0.2M Calcium
Chloride, 0.1M HEPES
pH 7.0, 24% PEG 400,
5% (v/v) glycerol,
0.1M TCEP
hydrochloride 0.2M Calcium
Chloride, 0.1M HEPES
pH 7.0, 24% PEG 400,
5% (v/v) glycerol, 2.0M
Sodium thiocyanate

SEQUENCE LISTING

```
<160> NUMBER OF SEQ ID NOS: 1

<210> SEQ ID NO 1
<211> LENGTH: 21
<212> TYPE: PRT
<213> ORGANISM: Homo sapiens

<400> SEQUENCE: 1

Leu Thr Pro Glu Glu Leu Lys Lys Phe Lys Met Lys Leu Gly Thr Val
1               5                   10                  15

Pro Leu Arg Glu Gly
            20
```

STRUCTURE-GUIDED ENGINEERING OF PEPTIDE-BASED NLRP3 INFLAMMASOME INHIBITORS FOR MYELODYSPLASTIC SYNDROMES (MDS)

This application is a United States National Phase Patent Application of International Patent Application Number PCT/US2020/030945, filed on May 1, 2020, which claims the benefit of U.S. Provisional Application No. 62/841,826, filed on May 1, 2019, applications which are incorporated herein by reference in their entireties.

This invention was made with government support under Grant No. CA204738 awarded by the National Institutes of Health. The government has certain rights in the invention.

I. BACKGROUND

1. The NLRP3 inflammasome contributes to innate immunity by sensing pathogenic microbes, and aberrant inflammasome activation is a hallmark of Myelodysplastic Syndrome (MDS). At the molecular level, the NLRP3 inflammasome is driven by interactions between the pyrin (PYD) domains of the NLRP3 sensor protein and the ASC adaptor protein. These interactions contribute to innate immunity by sensing pathogenic microbes. Aberrant activation is a hallmark of Myelodysplastic Syndrome (MDS), and induces clonal expansion and pyroptosis. What are needed are inflammasome inhibitors.

II. SUMMARY

2. Disclosed are methods and compositions related to engineered inhibitor of NLRP3.

3. In one aspect, disclosed herein are engineered inhibitors of NACHT, LRR and PYD domains-containing protein 3 (NLRP3) inflammasome comprising a Helix 2 of POP1 comprising one or more substitutions at residues 18, 21, 22, 25, 26, 28, 29, and/or 30 of POP1 as set forth in SEQ ID NO: 1. For example, disclose herein are engineered inhibitors of NLRP3 of any preceding aspect, wherein the amino acid at residue 18 comprises glutamic acid, glycine, lysine, glutamine, or arginine.

4. Also disclosed herein are engineered inhibitors of NLRP3 of any preceding aspect, wherein the substitution at residue 21 comprises lysine, leucine, methionine, glutamine, or arginine.

5. In one aspect, disclosed herein are engineered inhibitors of NLRP3 of any preceding aspect, wherein the amino acid at residue 22 comprises lysine, leucine, methionine, glutamine, or arginine.

6. Also disclosed herein are engineered inhibitors of NLRP3 of any preceding aspect, wherein the amino acid at residue 25 comprises aspartic acid, glutamic acid, phenylalanine, histidine, isoleucine, lysine, methionine, asparagine, glutamine, tyrosine, valine, or leucine.

7. In one aspect, disclosed herein are engineered inhibitors of any preceding aspect, wherein the amino acid at residue 26 comprises glutamic acid, glycine, lysine, leucine, methionine, glutamine, valine, or arginine.

8. Also disclosed herein are engineered inhibitors of NLRP3 of any preceding aspect, wherein the amino acid at residue 28 comprises aspartic acid, histidine, isoleucine, leucine, asparagine, or valine.

9. In one aspect, disclosed herein are engineered inhibitors of any preceding aspect, wherein the amino acid at residue 29 comprises cysteine, aspartic acid, phenylalanine, glycine, histidine, isoleucine, leucine, asparagine, arginine, serine, valine, or tyrosine.

10. Also disclosed herein are engineered inhibitors of NLRP3 of any preceding aspect, wherein the amino acid at residue 30 comprises alanine, aspartic acid, histidine, isoleucine, leucine, asparagine, proline, threonine, or valine.

11. In one aspect, disclosed herein are methods of structured guided engineering of an inhibitor of NLRP3 comprising expressing a MBP-NLRP3$^{PYD}$, subjecting the expressed protein to Nickel affinity (Ni-NTA) or size exclusion purification, and/or optimizing the peptide.

12. In one aspect, disclosed herein are methods of treating, inhibiting, reducing, decreasing, ameliorating, and/or preventing a cancer and/or metastasis in a subject comprising administering to the subject engineered inhibitors of NLRP3 inflammasome of any preceding aspect. For example, disclosed herein are methods of treating, inhibiting, reducing, decreasing, ameliorating, and/or preventing a cancer and/or metastasis in a subject comprising administering to the subject engineered inhibitors of NLRP3 inflammasome comprising a Helix 2 of POP1 comprising one or more substitutions at residues 18, 21, 22, 25, 26, 28, 29, and/or 30 of POP1 as set forth in SEQ ID NO: 1 (such as, for example, an engineered inhibitors of NLRP3 comprising a glutamic acid, glycine, lysine, glutamine, or arginine at residue 18; a lysine, leucine, methionine, glutamine, or arginine at residue 21; a lysine, leucine, methionine, glutamine, or arginine at residue 22; an aspartic acid, glutamic acid, phenylalanine, histidine, isoleucine, lysine, methionine, asparagine, glutamine, tyrosine, valine, or leucine at residue 25; a glutamic acid, glycine, lysine, leucine, methionine, glutamine, valine, or arginine at residue 26; an aspartic acid, histidine, isoleucine, leucine, asparagine, or valine at residue 28; a cysteine, aspartic acid, phenylalanine, glycine, histidine, isoleucine, leucine, asparagine, arginine, serine, valine, or tyrosine at residue 29; and/or an alanine, aspartic acid, histidine, isoleucine, leucine, asparagine, proline, threonine, or valine at residue 30.

III. BRIEF DESCRIPTION OF THE DRAWINGS

13. The accompanying drawings, which are incorporated in and constitute a part of this specification, illustrate several embodiments and together with the description illustrate the disclosed compositions and methods.

14. FIG. 1 shows a general diagram of an active NLRP3 inflammasome complex.

Figure 2:
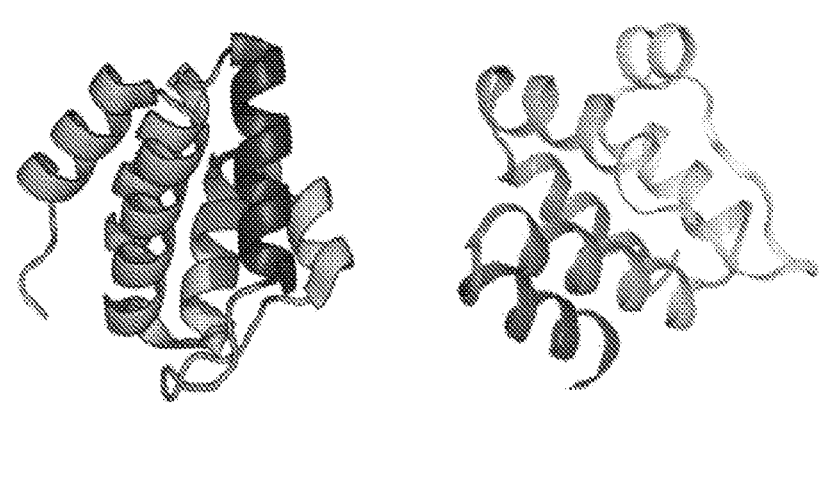

15. FIG. 2 shows Structures of NLRP3 PYD (PDB ID: 2NAQ) and ASC PYD (PDB ID: 1UCP) domains.

Figure 3:
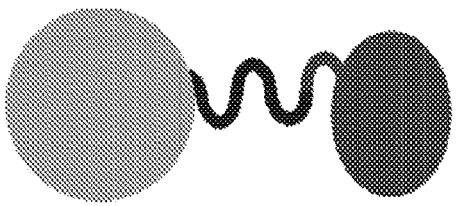

16. FIG. 3 shows schematic of a MBP-NLRP3$^{PYD}$ construct.

Figure 4:
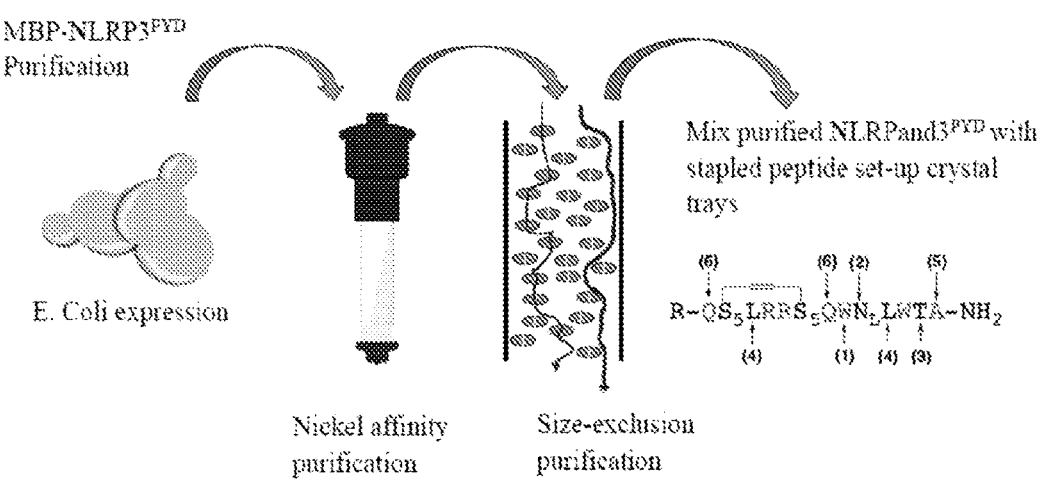

17. FIG. 4 shows crystallization strategy.

Figure 5:
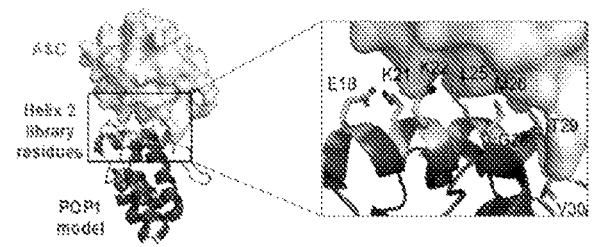

18. FIG. 5 shows a schematic of the contact residues of POP1 that interact with ASC$^{PYD}$.

Figure 6A:
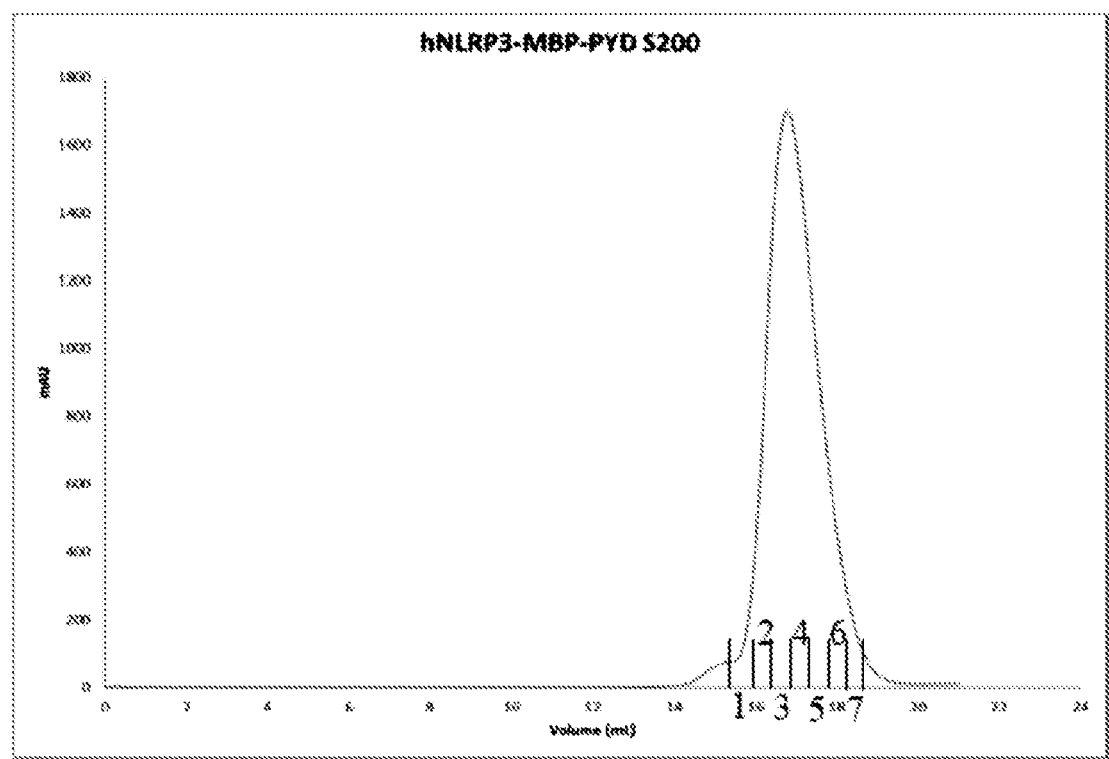
Figure 6B:
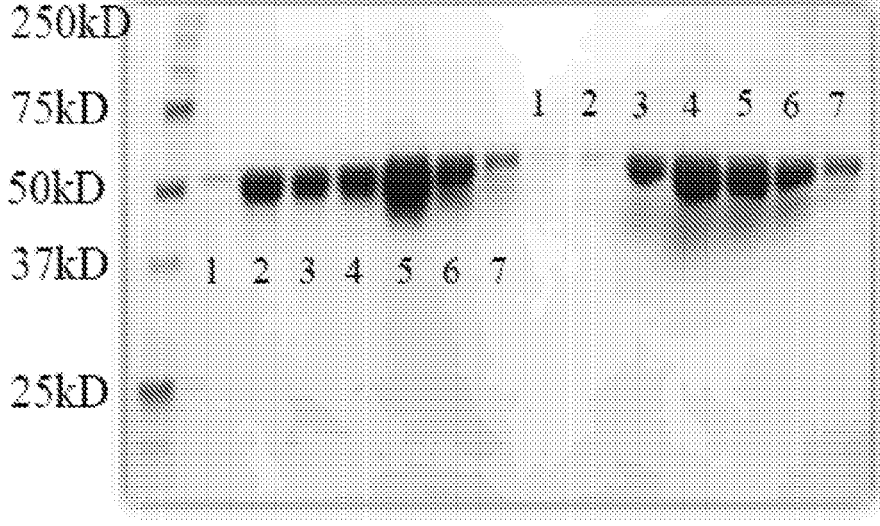

19. FIGS. 6A and 6B show Size exclusion chromatogram of MBP-NLRP3$^{PYD}$ (6A) and protein gel profiling the peaks (6B).

Figure 7:
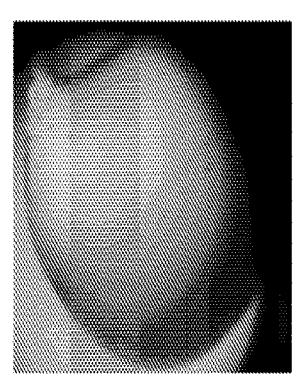
Figure 7:
Figure 7:
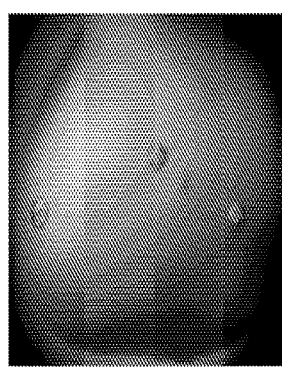
Figure 7:
Figure 7:
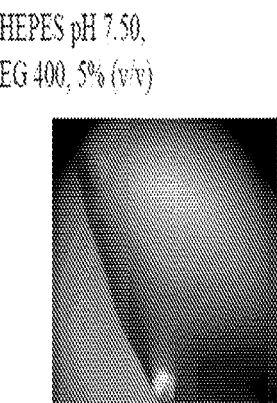
Figure 7:
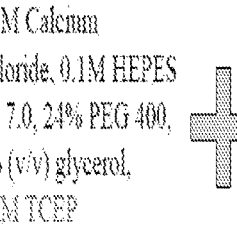
Figure 7:
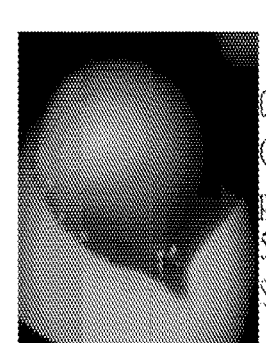
Figure 7:
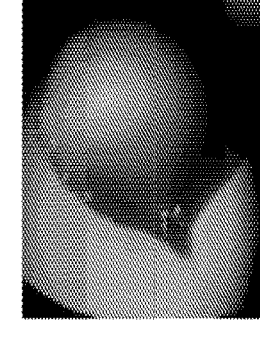

20. FIG. 7 shows Crystal trays of NLRP3$^{PYD}$. Far left is a condition that provides crystals. The middle is an optimized screen for pH, glycerol, and PEG. The far right is an optimized screen for additives.

Figure 8:
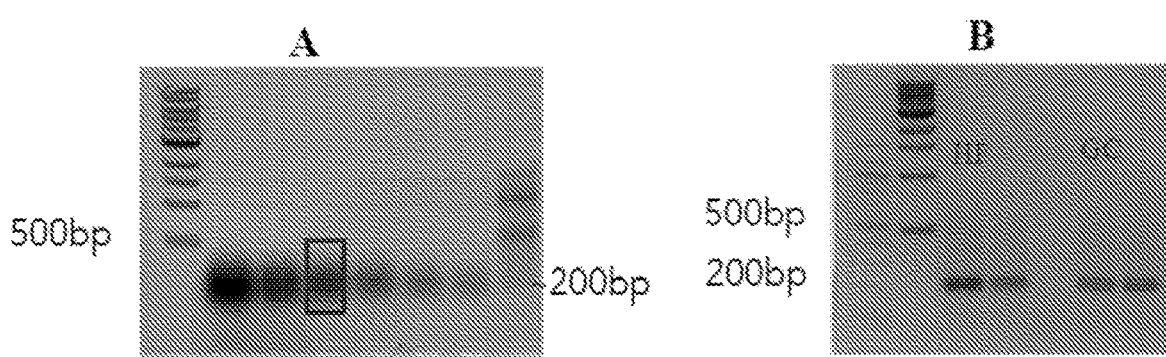

21. FIG. 8 shows assembly PCR (A) and amplification (B) of degenerate primers.

IV. DETAILED DESCRIPTION

22. Before the present compounds, compositions, articles, devices, and/or methods are disclosed and described, it is to be understood that they are not limited to specific synthetic methods or specific recombinant biotechnology methods unless otherwise specified, or to particular reagents unless otherwise specified, as such may, of course, vary. It is also to be understood that the terminology used herein is for the purpose of describing particular embodiments only and is not intended to be limiting.

A. Definitions

As used in the specification and the appended claims, the singular forms "a," "an" and "the" include plural referents unless the context clearly dictates otherwise. Thus, for example, reference to "a pharmaceutical carrier" includes mixtures of two or more such carriers, and the like.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed the "less than or equal to 10" as well as "greater than or equal to 10" is also disclosed. It is also understood that the throughout the application, data is provided in a number of different formats, and that this data, represents endpoints and starting points, and ranges for any combination of the data points. For example, if a particular data point "10" and a particular data point 15 are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

"Optional" or "optionally" means that the subsequently described event or circumstance may or may not occur, and that the description includes instances where said event or circumstance occurs and instances where it does not.

A "decrease" can refer to any change that results in a smaller amount of a symptom, disease, composition, condition, or activity. A substance is also understood to decrease the genetic output of a gene when the genetic output of the gene product with the substance is less relative to the output of the gene product without the substance. Also for example, a decrease can be a change in the symptoms of a disorder such that the symptoms are less than previously observed. A decrease can be any individual, median, or average decrease in a condition, symptom, activity, composition in a statistically significant amount. Thus, the decrease can be a 1, 2, 3, 4, 5, 6, 7, 8, 9, 10, 15, 20, 25, 30, 35, 40, 45, 50, 55, 60, 65, 70, 75, 80, 85, 90, 95, or 100% decrease so long as the decrease is statistically significant.

"Inhibit," "inhibiting," and "inhibition" mean to decrease an activity, response, condition, disease, or other biological parameter. This can include but is not limited to the complete ablation of the activity, response, condition, or disease. This may also include, for example, a 10% reduction in the activity, response, condition, or disease as compared to the native or control level. Thus, the reduction can be a 10, 20, 30, 40, 50, 60, 70, 80, 90, 100%, or any amount of reduction in between as compared to native or control levels.

By "reduce" or other forms of the word, such as "reducing" or "reduction," is meant lowering of an event or characteristic (e.g., tumor growth). It is understood that this is typically in relation to some standard or expected value, in other words it is relative, but that it is not always necessary for the standard or relative value to be referred to. For example, "reduces tumor growth" means reducing the rate of growth of a tumor relative to a standard or a control.

"Treat," "treating," "treatment," and grammatical variations thereof as used herein, include the administration of a composition with the intent or purpose of partially or completely preventing, delaying, curing, healing, alleviating, relieving, altering, remedying, ameliorating, improving, stabilizing, mitigating, and/or reducing the intensity or frequency of one or more a diseases or conditions, a symptom of a disease or condition, or an underlying cause of a disease or condition. Treatments according to the invention may be applied preventively, prophylactically, palliatively or remedially. Prophylactic treatments are administered to a subject prior to onset (e.g., before obvious signs of cancer), during early onset (e.g., upon initial signs and symptoms of cancer), or after an established development of cancer. Prophylactic administration can occur for day(s) to years prior to the manifestation of symptoms of an infection.

By "prevent" or other forms of the word, such as "preventing" or "prevention," is meant to stop a particular event or characteristic, to stabilize or delay the development or progression of a particular event or characteristic, or to minimize the chances that a particular event or characteristic will occur. Prevent does not require comparison to a control as it is typically more absolute than, for example, reduce. As used herein, something could be reduced but not prevented, but something that is reduced could also be prevented. Likewise, something could be prevented but not reduced, but something that is prevented could also be reduced. It is understood that where reduce or prevent are used, unless specifically indicated otherwise, the use of the other word is also expressly disclosed.

"Biocompatible" generally refers to a material and any metabolites or degradation products thereof that are generally non-toxic to the recipient and do not cause significant adverse effects to the subject.

"Comprising" is intended to mean that the compositions, methods, etc. include the recited elements, but do not exclude others. "Consisting essentially of" when used to define compositions and methods, shall mean including the recited elements, but excluding other elements of any essential significance to the combination. Thus, a composition consisting essentially of the elements as defined herein would not exclude trace contaminants from the isolation and purification method and pharmaceutically acceptable carriers, such as phosphate buffered saline, preservatives, and the like. "Consisting of" shall mean excluding more than trace elements of other ingredients and substantial method steps for administering the compositions provided and/or claimed in this disclosure. Embodiments defined by each of these transition terms are within the scope of this disclosure.

A "control" is an alternative subject or sample used in an experiment for comparison purposes. A control can be "positive" or "negative."

The term "subject" refers to any individual who is the target of administration or treatment. The subject can be a vertebrate, for example, a mammal. In one aspect, the subject can be human, non-human primate, bovine, equine, porcine, canine, or feline. The subject can also be a guinea pig, rat, hamster, rabbit, mouse, or mole. Thus, the subject can be a human or veterinary patient. The term "patient" refers to a subject under the treatment of a clinician, e.g., physician.

"Effective amount" of an agent refers to a sufficient amount of an agent to provide a desired effect. The amount of agent that is "effective" will vary from subject to subject, depending on many factors such as the age and general condition of the subject, the particular agent or agents, and the like. Thus, it is not always possible to specify a quantified "effective amount." However, an appropriate "effective amount" in any subject case may be determined by one of ordinary skill in the art using routine experimentation. Also, as used herein, and unless specifically stated otherwise, an "effective amount" of an agent can also refer to an amount covering both therapeutically effective amounts and prophylactically effective amounts. An "effective amount" of an agent necessary to achieve a therapeutic effect may vary according to factors such as the age, sex, and weight of the subject. Dosage regimens can be adjusted to provide the optimum therapeutic response. For example, several divided doses may be administered daily or the dose may be proportionally reduced as indicated by the exigencies of the therapeutic situation.

A "pharmaceutically acceptable" component can refer to a component that is not biologically or otherwise undesirable, i.e., the component may be incorporated into a pharmaceutical formulation provided by the disclosure and administered to a subject as described herein without causing significant undesirable biological effects or interacting in a deleterious manner with any of the other components of the formulation in which it is contained. When used in reference to administration to a human, the term generally implies the component has met the required standards of toxicological and manufacturing testing or that it is included on the Inactive Ingredient Guide prepared by the U.S. Food and Drug Administration.

"Pharmaceutically acceptable carrier" (sometimes referred to as a "carrier") means a carrier or excipient that is useful in preparing a pharmaceutical or therapeutic composition that is generally safe and non-toxic and includes a carrier that is acceptable for veterinary and/or human pharmaceutical or therapeutic use. The terms "carrier" or "pharmaceutically acceptable carrier" can include, but are not limited to, phosphate buffered saline solution, water, emulsions (such as an oil/water or water/oil emulsion) and/or various types of wetting agents. As used herein, the term "carrier" encompasses, but is not limited to, any excipient, diluent, filler, salt, buffer, stabilizer, solubilizer, lipid, stabilizer, or other material well known in the art for use in pharmaceutical formulations and as described further herein.

"Pharmacologically active" (or simply "active"), as in a "pharmacologically active" derivative or analog, can refer to a derivative or analog (e.g., a salt, ester, amide, conjugate, metabolite, isomer, fragment, etc.) having the same type of pharmacological activity as the parent compound and approximately equivalent in degree.

"Therapeutic agent" refers to any composition that has a beneficial biological effect. Beneficial biological effects include both therapeutic effects, e.g., treatment of a disorder or other undesirable physiological condition, and prophylactic effects, e.g., prevention of a disorder or other undesirable physiological condition (e.g., a non-immunogenic cancer). The terms also encompass pharmaceutically acceptable, pharmacologically active derivatives of beneficial agents specifically mentioned herein, including, but not limited to, salts, esters, amides, proagents, active metabolites, isomers, fragments, analogs, and the like. When the terms "therapeutic agent" is used, then, or when a particular agent is specifically identified, it is to be understood that the term includes the agent per se as well as pharmaceutically acceptable, pharmacologically active salts, esters, amides, proagents, conjugates, active metabolites, isomers, fragments, analogs, etc.

"Therapeutically effective amount" or "therapeutically effective dose" of a composition (e.g. a composition comprising an agent) refers to an amount that is effective to achieve a desired therapeutic result. In some embodiments, a desired therapeutic result is the control of type I diabetes. In some embodiments, a desired therapeutic result is the control of obesity. Therapeutically effective amounts of a given therapeutic agent will typically vary with respect to factors such as the type and severity of the disorder or disease being treated and the age, gender, and weight of the subject. The term can also refer to an amount of a therapeutic agent, or a rate of delivery of a therapeutic agent (e.g., amount over time), effective to facilitate a desired therapeutic effect, such as pain relief. The precise desired therapeutic effect will vary according to the condition to be treated, the tolerance of the subject, the agent and/or agent formulation to be administered (e.g., the potency of the therapeutic agent, the concentration of agent in the formulation, and the like), and a variety of other factors that are appreciated by those of ordinary skill in the art. In some instances, a desired biological or medical response is achieved following administration of multiple dosages of the composition to the subject over a period of days, weeks, or years.

The term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon.

B. Compositions

23. Disclosed are the components to be used to prepare the disclosed compositions as well as the compositions themselves to be used within the methods disclosed herein.

These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a particular peptide inhibitor is disclosed and discussed and a number of modifications that can be made to a number of molecules including the peptide inhibitor are discussed, specifically contemplated is each and every combination and permutation of peptide inhibitor and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods.

24. To guide the development of inflammasome inhibitors, we will (i) co-crystallize the NRLP3 PYD domain in complex with a stapled-peptide that binds to the ASC-binding interface and (ii) use directed evolution to generate high-affinity peptide inhibitors of ASC-NLRP3 interactions.

25. In one aspect, disclosed herein are engineered inhibitors of NACHT, LRR and PYD domains-containing protein 3 (NLRP3) inflammasome comprising a Helix 2 of POP1 comprising one or more substitutions at residues 18, 21, 22, 25, 26, 28, 29, and/or 30 of POP1 as set forth in SEQ ID NO: 1 and shown in Table 3. It is understood and herein contemplated that the any one or combination of the residues 18, 21, 22, 25, 26, 28, 29, and/or 30 can comprise a native residue (E18, K21, K22, M25, K26, G28, T29, or V30) or substitution at that residue. For example, disclose herein are engineered inhibitors of NLRP3, wherein the amino acid at residue 18 comprises glutamic acid (wild-type (WT)) or a substitution at residue 18 such as a glutamic acid to glycine (E18G) substitution, a glutamic acid to lysine (E18K) substitution, a glutamic acid to glutamine (E18Q) substitution, or a glutamic acid to arginine (E18R) substitution. Also disclosed herein are engineered inhibitors of NLRP3, wherein the amino acid at residue 21 comprises lysine (WT), or a substitution at residue 21 such as a lysine to leucine ((K21L) substitution, a lysine to methionine (K21M) substitution, a lysine to glutamine substitution (K21Q), or a lysine to arginine (K21R) substitution. In one aspect, disclosed herein are engineered inhibitors of NLRP3, wherein the amino acid at residue 22 comprises lysine (WT), or a substitution at residue 22 such as a lysine to leucine ((K22L) substitution, a lysine to methionine (K22M) substitution, a lysine to glutamine substitution (K22Q), or a lysine to arginine (K22R) substitution. Also disclosed herein are engineered inhibitors of NLRP3, wherein the amino acid at residue 25 comprises a methionine (WT) or a substitution at residue 25 such as a methionine to aspartic acid (M25D) substitution, methionine to glutamic acid (M25E) substitution, methionine to phenylalanine (M25F) substitution, methionine to histidine (M25H) substitution, methionine to isoleucine (M25I) substitution, methionine to lysine (M25K) substitution, methionine to asparagine (M25N) substitution, methionine to glutamine (M25Q) substitution, methionine to tyrosine (M25Y) substitution, methionine to valine (M25V) substitution, or methionine to leucine (M25L) substitution. In one aspect, disclosed herein are engineered inhibitors of any preceding aspect, wherein the amino acid at residue 26 comprises a lysine (WT) or a substitution at residue 26 such as a lysine to glutamic acid (K26E) substitution, lysine to glycine (K26G) substitution, lysine to leucine (K26L) substitution, lysine to methionine (K26M) substitution, lysine to glutamine (K26Q) substitution, lysine to valine (K26V) substitution, or lysine to arginine (K26R) substitution.

26. Also disclosed herein are engineered inhibitors of any preceding aspect, wherein the amino acid at residue 28 comprises a glysine (WT) or a substitution at residue 28 such as a glysine to aspartic acid (G28D) substitution, a glysine to histidine (G28H) substitution, a glysine to isoleucine (G28I) substitution, a glysine to leucine (G28L) substitution, a glysine to asparagine (G28N) substitution, or a glysine to valine (G28V) substitution. In one aspect, disclosed herein are engineered inhibitors of any preceding aspect, wherein the amino acid at residue 29 comprises a threonine (WT) or a substitution at residue 29 such as a threonine to cysteine (T29C) substitution, a threonine to aspartic acid (T29D) substitution, a threonine to phenylalanine (T29F) substitution, a threonine to glycine (T29G) substitution, a threonine to histidine (T29H) substitution, a threonine to isoleucine (T29I) substitution, a threonine to leucine (T29L) substitution, a threonine to asparagine (T29N) substitution, a threonine to arginine (T29R) substitution, a threonine to serine (T29S) substitution, a threonine to valine (T29V) substitution, or a threonine to tyrosine (T29Y) substitution. Also disclosed herein are engineered inhibitors of any preceding aspect, wherein the amino acid at residue 30 comprises a valine (WT) or a substitution at residue 29 such as a valine to alanine (V30A) substitution, a valine to aspartic acid (V30D) substitution, a valine to histidine (V30H) substitution, a valine to isoleucine (V30I) substitution, a valine to leucine (V30L) substitution, a valine to asparagine (V30N) substitution, a valine to proline (V30P) substitution, or a valine to threonine (V30T) substitution.

27. In one aspect, disclosed herein are methods of structured guided engineering of an inhibitor of NLRP3 comprising expressing a MBP-NLRP3$^{PYD}$, subjecting the expressed protein to Nickel affinity (Ni-NTA) or size exclusion purification, and/or optimizing the peptide.

1. Homology/identity (Version 1)

28. It is understood that one way to define any known variants and derivatives or those that might arise, of the disclosed genes and proteins herein is through defining the variants and derivatives in terms of homology to specific known sequences. Specifically disclosed are variants of these and other genes and proteins herein disclosed which have at least, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 percent homology to the stated sequence. Those of skill in the art readily understand how to determine the homology of two proteins or nucleic acids, such as genes. For example, the homology can be calculated after aligning the two sequences so that the homology is at its highest level.

29. Another way of calculating homology can be performed by published algorithms. Optimal alignment of sequences for comparison may be conducted by the local homology algorithm of Smith and Waterman *Adv. Appl. Math.* 2: 482 (1981), by the homology alignment algorithm of Needleman and Wunsch, *J. MoL Biol.* 48: 443 (1970), by the search for similarity method of Pearson and Lipman, *Proc. Natl. Acad. Sci. U.S.A.* 85: 2444 (1988), by computerized implementations of these algorithms (GAP, BEST-FIT, FASTA, and TFASTA in the Wisconsin Genetics Software Package, Genetics Computer Group, 575 Science Dr., Madison, Wis.), or by inspection.

30. The same types of homology can be obtained for nucleic acids by for example the algorithms disclosed in Zuker, M. *Science* 244:48-52, 1989, Jaeger et al. *Proc. Natl. Acad. Sci. USA* 86:7706-7710, 1989, Jaeger et al. *Methods Enzymol.* 183:281-306, 1989 which are herein incorporated by reference for at least material related to nucleic acid alignment.

2. Peptides a) Protein Variants

31. As discussed herein there are numerous variants that are known and herein contemplated. In addition, to the known functional strain variants there are derivatives of the disclosed proteins which also function in the disclosed methods and compositions. Protein variants and derivatives are well understood to those of skill in the art and in can involve amino acid sequence modifications. For example, amino acid sequence modifications typically fall into one or more of three classes: substitutional, insertional or deletional variants. Insertions include amino and/or carboxyl terminal fusions as well as intrasequence insertions of single or multiple amino acid residues. Insertions ordinarily will be smaller insertions than those of amino or carboxyl terminal fusions, for example, on the order of one to four residues Immunogenic fusion protein derivatives, such as those described in the examples, are made by fusing a polypeptide sufficiently large to confer immunogenicity to the target sequence by cross-linking in vitro or by recombinant cell culture transformed with DNA encoding the fusion. Deletions are characterized by the removal of one or more amino acid residues from the protein sequence. Typically, no more than from about 2 to 6 residues are deleted at any one site within the protein molecule. These variants ordinarily are prepared by site specific mutagenesis of nucleotides in the DNA encoding the protein, thereby producing DNA encoding the variant, and thereafter expressing the DNA in recombinant cell culture. Techniques for making substitution mutations at predetermined sites in DNA having a known sequence are well known, for example M13 primer mutagenesis and PCR mutagenesis. Amino acid substitutions are typically of single residues, but can occur at a number of different locations at once; insertions usually will be on the order of about from 1 to 10 amino acid residues; and deletions will range about from 1 to 30 residues. Deletions or insertions preferably are made in adjacent pairs, i.e. a deletion of 2 residues or insertion of 2 residues. Substitutions, deletions, insertions or any combination thereof may be combined to arrive at a final construct. The mutations must not place the sequence out of reading frame and preferably will not create complementary regions that could produce secondary mRNA structure. Substitutional variants are those in which at least one residue has been removed and a different residue inserted in its place. Such substitutions generally are made in accordance with the following Tables 1 and 2 and are referred to as conservative substitutions.

TABLE 1

| Amino Acid Abbreviations | | |
| --- | --- | --- |
| Amino Acid | Abbreviations | |
| Alanine | Ala | A |
| allosoleucine | AIle | |
| Arginine | Arg | R |
| asparagine | Asn | N |
| aspartic acid | Asp | D |
| Cysteine | Cys | C |
| glutamic acid | Glu | E |
| Glutamine | Gln | Q |
| Glycine | Gly | G |
| Histidine | His | H |
| Isolelucine | Ile | I |
| Leucine | Leu | L |
| Lysine | Lys | K |
| phenylalanine | Phe | F |
| proline | Pro | P |
| pyroglutamic acid | pGlu | |
| Serine | Ser | S |
| Threonine | Thr | T |
| Tyrosine | Tyr | Y |
| Tryptophan | Trp | W |
| Valine | Val | V |

TABLE 2

| Amino Acid Substitutions Original Residue Exemplary Conservative Substitutions, others are known in the art. | |
| --- | --- |
| Ala | Ser |
| Arg | Lys; Gln |
| Asn | Gln; His |
| Asp | Glu |
| Cys | Ser |
| Gln | Asn, Lys |
| Glu | Asp |
| Gly | Pro |
| His | Asn; Gln |
| Ile | Leu; Val |
| Leu | Ile; Val |
| Lys | Arg; Gln |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

32. Substantial changes in function or immunological identity are made by selecting substitutions that are less conservative than those in Table 2, i.e., selecting residues that differ more significantly in their effect on maintaining (a) the structure of the polypeptide backbone in the area of the substitution, for example as a sheet or helical conformation, (b) the charge or hydrophobicity of the molecule at the target site or (c) the bulk of the side chain. The substitutions which in general are expected to produce the greatest changes in the protein properties will be those in which (a) a hydrophilic residue, e.g. seryl or threonyl, is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g., lysyl, arginyl, or histidyl, is substituted for (or by) an electronegative residue, e.g., glutamyl or aspartyl; or (d) a residue having a bulky side chain, e.g., phenylalanine, is substituted for (or by) one not having a side chain, e.g., glycine, in this case, (e) by increasing the number of sites for sulfation and/or glycosylation.

33. For example, the replacement of one amino acid residue with another that is biologically and/or chemically similar is known to those skilled in the art as a conservative substitution. For example, a conservative substitution would be replacing one hydrophobic residue for another, or one polar residue for another. The substitutions include combinations such as, for example, Gly, Ala; Val, Ile, Leu; Asp, Glu; Asn, Gln; Ser, Thr; Lys, Arg; and Phe, Tyr. Such conservatively substituted variations of each explicitly disclosed sequence are included within the mosaic polypeptides provided herein.

34. Substitutional or deletional mutagenesis can be employed to insert sites for N-glycosylation (Asn-X-Thr/Ser) or O-glycosylation (Ser or Thr). Deletions of cysteine or other labile residues also may be desirable. Deletions or substitutions of potential proteolysis sites, e.g. Arg, is accomplished for example by deleting one of the basic residues or substituting one by glutaminyl or histidyl residues.

35. Certain post-translational derivatizations are the result of the action of recombinant host cells on the expressed polypeptide. Glutaminyl and asparaginyl residues are frequently post-translationally deamidated to the corresponding glutamyl and asparyl residues. Alternatively, these residues are deamidated under mildly acidic conditions. Other post-translational modifications include hydroxylation of proline and lysine, phosphorylation of hydroxyl groups of seryl or threonyl residues, methylation of the o-amino groups of lysine, arginine, and histidine side chains (T. E. Creighton, Proteins: Structure and Molecular Properties, W. H. Freeman & Co., San Francisco pp 79-86 [1983]), acetylation of the N-terminal amine and, in some instances, amidation of the C-terminal carboxyl.

36. It is understood that one way to define the variants and derivatives of the disclosed proteins herein is through defining the variants and derivatives in terms of homology/identity to specific known sequences. Specifically disclosed are variants of these and other proteins herein disclosed which have at least, 70% or 75% or 80% or 85% or 90% or 95% homology to the stated sequence. Those of skill in the art readily understand how to determine the homology of two proteins. For example, the homology can be calculated after aligning the two sequences so that the homology is at its highest level.

37. Another way of calculating homology can be performed by published algorithms. Optimal alignment of sequences for comparison may be conducted by the local homology algorithm of Smith and Waterman *Adv. Appl. Math.* 2: 482 (1981), by the homology alignment algorithm of Needleman and Wunsch, *J. MoL Biol.* 48: 443 (1970), by the search for similarity method of Pearson and Lipman, *Proc. Natl. Acad. Sci. U.S.A.* 85: 2444 (1988), by computerized implementations of these algorithms (GAP, BEST-FIT, FASTA, and TFASTA in the Wisconsin Genetics Software Package, Genetics Computer Group, 575 Science Dr., Madison, Wis.), or by inspection.

38. The same types of homology can be obtained for nucleic acids by for example the algorithms disclosed in Zuker, M. *Science* 244:48-52, 1989, Jaeger et al. *Proc. Natl. Acad. Sci. USA* 86:7706-7710, 1989, Jaeger et al. *Methods Enzymol.* 183:281-306, 1989.

39. It is understood that the description of conservative mutations and homology can be combined together in any combination, such as embodiments that have at least 70% homology to a particular sequence wherein the variants are conservative mutations.

40. As this specification discusses various proteins and protein sequences it is understood that the nucleic acids that can encode those protein sequences are also disclosed. This would include all degenerate sequences related to a specific protein sequence, i.e. all nucleic acids having a sequence that encodes one particular protein sequence as well as all nucleic acids, including degenerate nucleic acids, encoding the disclosed variants and derivatives of the protein sequences. Thus, while each particular nucleic acid sequence may not be written out herein, it is understood that each and every sequence is in fact disclosed and described herein through the disclosed protein sequence. It is also understood that while no amino acid sequence indicates what particular DNA sequence encodes that protein within an organism, where particular variants of a disclosed protein are disclosed herein, the known nucleic acid sequence that encodes that protein i is also known and herein disclosed and described.

41. It is understood that there are numerous amino acid and peptide analogs which can be incorporated into the disclosed compositions. For example, there are numerous D amino acids or amino acids which have a different functional substituent then the amino acids shown in Table 1 and Table 2. The opposite stereo isomers of naturally occurring peptides are disclosed, as well as the stereo isomers of peptide analogs. These amino acids can readily be incorporated into polypeptide chains by charging tRNA molecules with the amino acid of choice and engineering genetic constructs that utilize, for example, amber codons, to insert the analog amino acid into a peptide chain in a site specific way.

42. Molecules can be produced that resemble peptides, but which are not connected via a natural peptide linkage. For example, linkages for amino acids or amino acid analogs can include $CH_2NH$—, —$CH_2S$—, —$CH_2$—$CH_2$—, —$CH$=$CH$— (cis and trans), —$COCH_2$—, —$CH(OH)$ $CH_2$—, and —$CHH_2SO$—(These and others can be found in Spatola, A. F. in *Chemistry and Biochemistry of Amino Acids, Peptides, and Proteins,* B. Weinstein, eds., Marcel Dekker, New York, p. 267 (1983); Spatola, A. F., *Vega Data* (March 1983), Vol. 1, Issue 3, Peptide Backbone Modifications (general review); Morley, *Trends Pharm Sci* (1980) pp. 463-468; Hudson, D. et al., Int J Pept Prot Res 14:177-185 (1979) (—$CH_2NH$—, $CH_2CH_2$—); Spatola et al. *Life Sci* 38:1243-1249 (1986) (—$CH$ $H_2$—S); Hann *J. Chem. Soc Perkin Trans.* I 307-314 (1982) (—$CH$—$CH$—, cis and trans); Almquist et al. *J. Med. Chem.* 23:1392-1398 (1980) (—$COCH_2$—); Jennings-White et al. *Tetrahedron Lett* 23:2533 (1982) (—$COCH_2$—); Szelke et al. European Appln, EP 45665 CA (1982): 97:39405 (1982) (—$CH(OH)$ $CH_2$—); Holladay et al. *Tetrahedron.* Lett 24:4401-4404 (1983) (—$C(OH)CH_2$—); and Hruby *Life Sci* 31:189-199 (1982) (—$CH_2$—S—); each of which is incorporated herein by reference. A particularly preferred non-peptide linkage is —$CH_2NH$—. It is understood that peptide analogs can have more than one atom between the bond atoms, such as b-alanine, g-aminobutyric acid, and the like.

43 Amino acid analogs and analogs and peptide analogs often have enhanced or desirable properties, such as, more economical production, greater chemical stability, enhanced pharmacological properties (half-life, absorption, potency, efficacy, etc.), altered specificity (e.g., a broad-spectrum of biological activities), reduced antigenicity, and others.

44. D-amino acids can be used to generate more stable peptides, because D amino acids are not recognized by peptidases and such. Systematic substitution of one or more amino acids of a consensus sequence with a D-amino acid of the same type (e.g., D-lysine in place of L-lysine) can be used to generate more stable peptides. Cysteine residues can be used to cyclize or attach two or more peptides together. This can be beneficial to constrain peptides into particular conformations.

3. Pharmaceutical Carriers/Delivery of Pharmaceutical Products

45. As described above, the compositions can also be administered in vivo in a pharmaceutically acceptable carrier. By "pharmaceutically acceptable" is meant a material that is not biologically or otherwise undesirable, i.e., the material may be administered to a subject, along with the nucleic acid or vector, without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art.

46. The compositions may be administered orally, parenterally (e.g., intravenously), by intramuscular injection, by intraperitoneal injection, transdermally, extracorporeally, topically or the like, including topical intranasal administration or administration by inhalant. As used herein, "topical intranasal administration" means delivery of the compositions into the nose and nasal passages through one or both of the nares and can comprise delivery by a spraying mechanism or droplet mechanism, or through aerosolization of the nucleic acid or vector. Administration of the compositions by inhalant can be through the nose or mouth via delivery by a spraying or droplet mechanism. Delivery can also be directly to any area of the respiratory system (e.g., lungs) via intubation. The exact amount of the compositions required will vary from subject to subject, depending on the species, age, weight and general condition of the subject, the severity of the allergic disorder being treated, the particular nucleic acid or vector used, its mode of administration and the like. Thus, it is not possible to specify an exact amount for every composition. However, an appropriate amount can be determined by one of ordinary skill in the art using only routine experimentation given the teachings herein.

47. Parenteral administration of the composition, if used, is generally characterized by injection. Injectables can be prepared in conventional forms, either as liquid solutions or suspensions, solid forms suitable for solution of suspension in liquid prior to injection, or as emulsions. A more recently revised approach for parenteral administration involves use of a slow release or sustained release system such that a constant dosage is maintained. See, e.g., U.S. Pat. No. 3,610,795, which is incorporated by reference herein.

48. The materials may be in solution, suspension (for example, incorporated into microparticles, liposomes, or cells). These may be targeted to a particular cell type via antibodies, receptors, or receptor ligands. The following references are examples of the use of this technology to target specific proteins to tumor tissue (Senter, et al., *Bioconjugate Chem.,* 2:447-451, (1991); Bagshawe, K. D., *Br. J. Cancer,* 60:275-281, (1989); Bagshawe, et al., *Br. J. Cancer,* 58:700-703, (1988); Senter, et al., *Bioconjugate Chem.,* 4:3-9, (1993); Battelli, et al., *Cancer Immunol. Immunother.,* 35:421-425, (1992); Pietersz and McKenzie, *Immunolog. Reviews,* 129:57-80, (1992); and Roffler, et al., *Biochem. Pharmacol,* 42:2062-2065, (1991)). Vehicles such as "stealth" and other antibody conjugated liposomes (including lipid mediated drug targeting to colonic carcinoma), receptor mediated targeting of DNA through cell specific ligands, lymphocyte directed tumor targeting, and highly specific therapeutic retroviral targeting of murine glioma cells in vivo. The following references are examples of the use of this technology to target specific proteins to tumor tissue (Hughes et al., *Cancer Research,* 49:6214-6220, (1989); and Litzinger and Huang, *Biochimica et Biophysica Acta,* 1104:179-187, (1992)). In general, receptors are involved in pathways of endocytosis, either constitutive or ligand induced. These receptors cluster in clathrin-coated pits, enter the cell via clathrin-coated vesicles, pass through an acidified endosome in which the receptors are sorted, and then either recycle to the cell surface, become stored intracellularly, or are degraded in lysosomes. The internalization pathways serve a variety of functions, such as nutrient uptake, removal of activated proteins, clearance of macromolecules, opportunistic entry of viruses and toxins, dissociation and degradation of ligand, and receptor-level regulation. Many receptors follow more than one intracellular pathway, depending on the cell type, receptor concentration, type of ligand, ligand valency, and ligand concentration. Molecular and cellular mechanisms of receptor-mediated endocytosis has been reviewed (Brown and Greene, *DNA and Cell Biology* 10:6, 399-409 (1991)).

a) Pharmaceutically Acceptable Carriers

49. The compositions, including antibodies, can be used therapeutically in combination with a pharmaceutically acceptable carrier.

50. Suitable carriers and their formulations are described in *Remington: The Science and Practice of Pharmacy* (19th ed.) ed. A. R. Gennaro, Mack Publishing Company, Easton, Pa. 1995. Typically, an appropriate amount of a pharmaceutically-acceptable salt is used in the formulation to render the formulation isotonic. Examples of the pharmaceutically-acceptable carrier include, but are not limited to, saline, Ringer's solution and dextrose solution. The pH of the solution is preferably from about 5 to about 8, and more preferably from about 7 to about 7.5. Further carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers may be more preferable depending upon, for instance, the route of administration and concentration of composition being administered.

51. Pharmaceutical carriers are known to those skilled in the art. These most typically would be standard carriers for administration of drugs to humans, including solutions such as sterile water, saline, and buffered solutions at physiological pH. The compositions can be administered intramuscularly or subcutaneously. Other compounds will be administered according to standard procedures used by those skilled in the art.

52. Pharmaceutical compositions may include carriers, thickeners, diluents, buffers, preservatives, surface active agents and the like in addition to the molecule of choice. Pharmaceutical compositions may also include one or more active ingredients such as antimicrobial agents, antiinflammatory agents, anesthetics, and the like.

53. The pharmaceutical composition may be administered in a number of ways depending on whether local or systemic treatment is desired, and on the area to be treated. Administration may be topically (including ophthalmically, vaginally, rectally, intranasally), orally, by inhalation, or parenterally, for example by intravenous drip, subcutaneous, intraperitoneal or intramuscular injection. The disclosed antibodies can be administered intravenously, intraperitoneally, intramuscularly, subcutaneously, intracavity, or transdermally.

54. Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

55. Formulations for topical administration may include ointments, lotions, creams, gels, drops, suppositories, sprays, liquids and powders. Conventional pharmaceutical carriers, aqueous, powder or oily bases, thickeners and the like may be necessary or desirable.

56. Compositions for oral administration include powders or granules, suspensions or solutions in water or non-aqueous media, capsules, sachets, or tablets. Thickeners, flavorings, diluents, emulsifiers, dispersing aids or binders may be desirable.

57. Some of the compositions may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines b) Therapeutic Uses

58. Effective dosages and schedules for administering the compositions may be determined empirically, and making such determinations is within the skill in the art. The dosage ranges for the administration of the compositions are those large enough to produce the desired effect in which the symptoms of the disorder are effected. The dosage should not be so large as to cause adverse side effects, such as unwanted cross-reactions, anaphylactic reactions, and the like. Generally, the dosage will vary with the age, condition, sex and extent of the disease in the patient, route of administration, or whether other drugs are included in the regimen, and can be determined by one of skill in the art. The dosage can be adjusted by the individual physician in the event of any counterindications. Dosage can vary, and can be administered in one or more dose administrations daily, for one or several days. Guidance can be found in the literature for appropriate dosages for given classes of pharmaceutical products. For example, guidance in selecting appropriate doses for antibodies can be found in the literature on therapeutic uses of antibodies, e.g., *Handbook of Monoclonal Antibodies,* Ferrone et al., eds., Noges Publications, Park Ridge, N.J., (1985) ch. 22 and pp. 303-357; Smith et al., *Antibodies in Human Diagnosis and Therapy,*

Haber et al., eds., Raven Press, New York (1977) pp. 365-389. A typical daily dosage of the antibody used alone might range from about 1 μg/kg to up to 100 mg/kg of body weight or more per day, depending on the factors mentioned above.

C. Methods of Making the Compositions

59. The compositions disclosed herein and the compositions necessary to perform the disclosed methods can be made using any method known to those of skill in the art for that particular reagent or compound unless otherwise specifically noted.

1. Peptide Synthesis

60. One method of producing the disclosed proteins is to link two or more peptides or polypeptides together by protein chemistry techniques. For example, peptides or polypeptides can be chemically synthesized using currently available laboratory equipment using either Fmoc (9-fluorenylmethyloxycarbonyl) or Boc (tert-butyloxycarbonoyl) chemistry. (Applied Biosystems, Inc., Foster City, CA). One skilled in the art can readily appreciate that a peptide or polypeptide corresponding to the disclosed proteins, for example, can be synthesized by standard chemical reactions. For example, a peptide or polypeptide can be synthesized and not cleaved from its synthesis resin whereas the other fragment of a peptide or protein can be synthesized and subsequently cleaved from the resin, thereby exposing a terminal group which is functionally blocked on the other fragment. By peptide condensation reactions, these two fragments can be covalently joined via a peptide bond at their carboxyl and amino termini, respectively, to form an antibody, or fragment thereof. (Grant GA (1992) *Synthetic Peptides: A User Guide.* W.H. Freeman and Co., N.Y. (1992); Bodansky M and Trost B., Ed. (1993) Principles of Peptide Synthesis. Springer-Verlag Inc., NY (which is herein incorporated by reference at least for material related to peptide synthesis). Alternatively, the peptide or polypeptide is independently synthesized in vivo as described herein. Once isolated, these independent peptides or polypeptides may be linked to form a peptide or fragment thereof via similar peptide condensation reactions.

61. For example, enzymatic ligation of cloned or synthetic peptide segments allow relatively short peptide fragments to be joined to produce larger peptide fragments, polypeptides or whole protein domains (Abrahmsen L et al., *Biochemistry,* 30:4151 (1991)). Alternatively, native chemical ligation of synthetic peptides can be utilized to synthetically construct large peptides or polypeptides from shorter peptide fragments. This method consists of a two step chemical reaction (Dawson et al. Synthesis of Proteins by Native Chemical Ligation. Science, 266:776-779 (1994)). The first step is the chemoselective reaction of an unprotected synthetic peptide-thioester with another unprotected peptide segment containing an amino-terminal Cys residue to give a thioester-linked intermediate as the initial covalent product. Without a change in the reaction conditions, this intermediate undergoes spontaneous, rapid intramolecular reaction to form a native peptide bond at the ligation site (Baggiolini M et al. (1992) *FEBS Lett.* 307:97-101; Clark-Lewis I et al., *J. Biol. Chem.,* 269:16075 (1994); Clark-Lewis I et al., *Biochemistry,* 30:3128 (1991); Rajarathnam K et al., *Biochemistry* 33:6623-30 (1994)).

62. Alternatively, unprotected peptide segments are chemically linked where the bond formed between the peptide segments as a result of the chemical ligation is an unnatural (non-peptide) bond (Schnolzer, M et al. *Science*, 256:221 (1992)). This technique has been used to synthesize analogs of protein domains as well as large amounts of relatively pure proteins with full biological activity (deLisle Milton R C et al., *Techniques in Protein Chemistry IV*. Academic Press, New York, pp. 257-267 (1992)).

D. Methods of Treating a Cancer or Precancerous Syndrome

63. In one aspect, disclosed herein are methods of treating, inhibiting, reducing, decreasing, ameliorating, and/or preventing a cancer and/or metastasis in a subject comprising administering to the subject engineered inhibitors of NLRP3 inflammasome of any preceding aspect. For example, disclosed herein are methods of treating, inhibiting, reducing, decreasing, ameliorating, and/or preventing a cancer and/or metastasis in a subject comprising administering to the subject engineered inhibitors of NLRP3 inflammasome comprising a Helix 2 of POP1 comprising one or more substitutions at residues 18, 21, 22, 25, 26, 28, 29, and/or 30 of POP1 as set forth in SEQ ID NO: 1 (such as, for example, an engineered inhibitors of NLRP3 comprising a glutamic acid, glycine, lysine, glutamine, or arginine at residue 18; a lysine, leucine, methionine, glutamine, or arginine at residue 21; a lysine, leucine, methionine, glutamine, or arginine at residue 22; an aspartic acid, glutamic acid, phenylalanine, histidine, isoleucine, lysine, methionine, asparagine, glutamine, tyrosine, valine, or leucine at residue 25; a glutamic acid, glycine, lysine, leucine, methionine, glutamine, valine, or arginine at residue 26; an aspartic acid, histidine, isoleucine, leucine, asparagine, or valine at residue 28; a cysteine, aspartic acid, phenylalanine, glycine, histidine, isoleucine, leucine, asparagine, arginine, serine, valine, or tyrosine at residue 29; and/or an alanine, aspartic acid, histidine, isoleucine, leucine, asparagine, proline, threonine, or valine at residue 30.

64. The disclosed methods of treating, inhibiting, reducing, decreasing, ameliorating, and/or preventing a cancer and/or metastasis comprising administering any of the engineered inhibitors of NLRP3 inflammasome disclosed herein can be used to treat, reduce, inhibit, ameliorate, and/or prevent any disease where uncontrolled cellular proliferation occurs such as cancers and/or metastasis. A representative but non-limiting list of cancers that the disclosed compositions can be used to treat is the following: Myelodysplastic Syndrome (MDS), lymphoma, B cell lymphoma, T cell lymphoma, mycosis fungoides, Hodgkin's Disease, myeloid leukemia, bladder cancer, brain cancer, nervous system cancer, head and neck cancer, squamous cell carcinoma of head and neck, lung cancers such as small cell lung cancer and non-small cell lung cancer, neuroblastoma/glioblastoma, ovarian cancer, skin cancer, liver cancer, melanoma, squamous cell carcinomas of the mouth, throat, larynx, and lung, cervical cancer, cervical carcinoma, breast cancer, and epithelial cancer, renal cancer, genitourinary cancer, pulmonary cancer, esophageal carcinoma, head and neck carcinoma, large bowel cancer, hematopoietic cancers; testicular cancer; colon cancer, rectal cancer, prostatic cancer, or pancreatic cancer.

65. It is understood and herein contemplated that the disclosed methods of treating, preventing, inhibiting, ameliorating, and/or reducing a cancer and/or metastasis in a subject comprising administering any of the engineered inhibitors of NLRP3 inflammasome disclosed herein can further comprise the administration of any anti-cancer agent that would further aid in the reduction, inhibition, treatment, and/or elimination of the cancer or metastasis (such as, for example, gemcitabine). Anti-cancer agents that can be used in the disclosed bioresponsive hydrogels or as an additional therapeutic agent in addition to the disclosed pharmaceutical compositions, and/or bioresponsive hydrogel matrixes for the methods of reducing, inhibiting, treating, ameliorating, decreasing, preventing, and/or eliminating a cancer and/or metastasis in a subject disclosed herein can comprise any anti-cancer agent known in the art, the including, but not limited to Abemaciclib, Abiraterone Acetate, Abitrexate (Methotrexate), Abraxane (Paclitaxel Albumin-stabilized Nanoparticle Formulation), ABVD, ABVE, ABVE-PC, AC, AC-T, Adcetris (Brentuximab Vedotin), ADE, Ado-Trastuzumab Emtansine, Adriamycin (Doxorubicin Hydrochloride), Afatinib Dimaleate, Afinitor (Everolimus), Akynzeo (Netupitant and Palonosetron Hydrochloride), Aldara (Imiquimod), Aldesleukin, Alecensa (Alectinib), Alectinib, Alemtuzumab, Alimta (Pemetrexed Disodium), Aliqopa (Copanlisib Hydrochloride), Alkeran for Injection (Melphalan Hydrochloride), Alkeran Tablets (Melphalan), Aloxi (Palonosetron Hydrochloride), Alunbrig (Brigatinib), Ambochlorin (Chlorambucil), Amboclorin Chlorambucil), Amifostine, Aminolevulinic Acid, Anastrozole, Aprepitant, Aredia (Pamidronate Disodium), Arimidex (Anastrozole), Aromasin (Exemestane),Arranon (Nelarabine), Arsenic Trioxide, Arzerra (Ofatumumab), Asparaginase Erwinia chrysanthemi, Atezolizumab, Avastin (Bevacizumab), Avelumab, Axitinib, Azacitidine, Bavencio (Avelumab), BEACOPP, Becenum (Carmustine), Beleodaq (Belinostat), Belinostat, Bendamustine Hydrochloride, BEP, Besponsa (Inotuzumab Ozogamicin), Bevacizumab, Bexarotene, Bexxar (Tositumomab and Iodine I 131 Tositumomab), Bicalutamide, BiCNU (Carmustine), Bleomycin, Blinatumomab, Blincyto (Blinatumomab), Bortezomib, Bosulif (Bosutinib), Bosutinib, Brentuximab Vedotin, Brigatinib, BuMel, Busulfan, Busulfex (Busulfan), Cabazitaxel, Cabometyx (Cabozantinib-S-Malate), Cabozantinib-S-Malate, CAF, Campath (Alemtuzumab), Camptosar, (Irinotecan Hydrochloride), Capecitabine, CAPDX, Carac (Fluorouracil—Topical), Carboplatin, CARBOPLATIN-TAXOL, Carfilzomib, Carmubris (Carmustine), Carmustine, Carmustine Implant, Casodex (Bicalutamide), CEM, Ceritinib, Cerubidine (Daunorubicin Hydrochloride), Cervarix (Recombinant HPV Bivalent Vaccine), Cetuximab, CEV, Chlorambucil, CHLORAMBUCIL-PREDNISONE, CHOP, Cisplatin, Cladribine, Clafen (Cyclophosphamide), Clofarabine, Clofarex (Clofarabine), Clolar (Clofarabine), CMF, Cobimetinib, Cometriq (Cabozantinib-S-Malate), Copanlisib Hydrochloride, COPDAC, COPP, COPP-ABV, Cosmegen (Dactinomycin), Cotellic (Cobimetinib), Crizotinib, CVP, Cyclophosphamide, Cyfos (Ifosfamide), Cyramza (Ramucirumab), Cytarabine, Cytarabine Liposome, Cytosar-U (Cytarabine), Cytoxan (Cyclophosphamide), Dabrafenib, Dacarbazine, Dacogen (Decitabine), Dactinomycin, Daratumumab, Darzalex (Daratumumab), Dasatinib, Daunorubicin Hydrochloride, Daunorubicin Hydrochloride and Cytarabine Liposome, Decitabine, Defibrotide Sodium, Defitelio (Defibrotide Sodium), Degarelix, Denileukin Diftitox, Denosumab, DepoCyt (Cytarabine Liposome), Dexamethasone, Dexrazoxane Hydrochloride, Dinutuximab, Docetaxel, Doxil (Doxorubicin Hydrochloride Liposome), Doxorubicin Hydrochloride, Doxorubicin Hydrochloride Liposome, Dox-SL (Doxorubicin Hydrochloride Liposome), DTIC-Dome (Dacarbazine), Durvalumab, Efudex (Fluorouracil—Topical), Elitek (Rasburicase), Ellence (Epirubicin Hydrochloride), Elotuzumab, Eloxatin (Oxaliplatin), Eltrombopag Olamine, Emend (Aprepitant), Empliciti (Elotuzumab), Enasidenib Mesylate, Enzalutamide, Epirubicin Hydrochloride, EPOCH, Erbitux (Cetuximab), Eribulin Mesylate, Erivedge (Vismodegib), Erlotinib Hydrochloride, Erwinaze (Asparaginase Erwinia chrysanthemi), Ethyol (Amifostine), Etopophos (Etoposide Phosphate), Etoposide, Etoposide Phosphate, Evacet (Doxorubicin Hydrochloride Liposome), Everolimus, Evista, (Raloxifene Hydrochloride), Evomela (Melphalan Hydrochloride), Exemestane, 5-FU (Fluorouracil Injection), 5-FU (Fluorouracil—Topical), Fareston (Toremifene), Farydak (Panobinostat), Faslodex (Fulvestrant), FEC, Femara (Letrozole), Filgrastim, Fludara (Fludarabine Phosphate), Fludarabine Phosphate, Fluoroplex (Fluorouracil—Topical), Fluorouracil Injection, Fluorouracil—Topical, Flutamide, Folex (Methotrexate), Folex PFS (Methotrexate), FOLFIRI, FOLFIRI-BEVACIZUMAB, FOLFIRI-CETUXIMAB, FOLFIRINOX, FOLFOX, Folotyn (Pralatrexate), FU-LV, Fulvestrant, Gardasil (Recombinant HPV Quadrivalent Vaccine), Gardasil 9 (Recombinant HPV Nonavalent Vaccine), Gazyva (Obinutuzumab), Gefitinib, Gemcitabine Hydrochloride, GEMCITABINE-CISPLATIN, GEMCITABINE-OXALIPLATIN, Gemtuzumab Ozogamicin, Gemzar (Gemcitabine Hydrochloride), Gilotrif (Afatinib Dimaleate), Gleevec (Imatinib Mesylate), Gliadel (Carmustine Implant), Gliadel wafer (Carmustine Implant), Glucarpidase, Goserelin Acetate, Halaven (Eribulin Mesylate), Hemangeol (Propranolol Hydrochloride), Herceptin (Trastuzumab), HPV Bivalent Vaccine, Recombinant, HPV Nonavalent Vaccine, Recombinant, HPV Quadrivalent Vaccine, Recombinant, Hycamtin (Topotecan Hydrochloride), Hydrea (Hydroxyurea), Hydroxyurea, Hyper-CVAD, Ibrance (Palbociclib), Ibritumomab Tiuxetan, Ibrutinib, ICE, Iclusig (Ponatinib Hydrochloride), Idamycin (Idarubicin Hydrochloride), Idarubicin Hydrochloride, Idelalisib, Idhifa (Enasidenib Mesylate), Ifex (Ifosfamide), Ifosfamide, Ifosfamidum (Ifosfamide), IL-2 (Aldesleukin), Imatinib Mesylate, Imbruvica (Ibrutinib), Imfinzi (Durvalumab), Imiquimod, Imlygic (Talimogene Laherparepvec), Inlyta (Axitinib), Inotuzumab Ozogamicin, Interferon Alfa-2b, Recombinant, Interleukin-2 (Aldesleukin), Intron A (Recombinant Interferon Alfa-2b), Iodine I 131 Tositumomab and Tositumomab, Ipilimumab, Iressa (Gefitinib), Irinotecan Hydrochloride, Irinotecan Hydrochloride Liposome, Istodax (Romidepsin), Ixabepilone, Ixazomib Citrate, Ixempra (Ixabepilone), Jakafi (Ruxolitinib Phosphate), JEB, Jevtana (Cabazitaxel), Kadcyla (Ado-Trastuzumab Emtansine), Keoxifene (Raloxifene Hydrochloride), Kepivance (Palifermin), Keytruda (Pembrolizumab), Kisqali (Ribociclib), Kymriah (Tisagenlecleucel), Kyprolis (Carfilzomib), Lanreotide Acetate, Lapatinib Ditosylate, Lartruvo (Olaratumab), Lenalidomide, Lenvatinib Mesylate, Lenvima (Lenvatinib Mesylate), Letrozole, Leucovorin Calcium, Leukeran (Chlorambucil), Leuprolide Acetate, Leustatin (Cladribine), Levulan (Aminolevulinic Acid), Linfolizin (Chlorambucil), LipoDox (Doxorubicin Hydrochloride Liposome), Lomustine, Lonsurf (Trifluridine and Tipiracil Hydrochloride), Lupron (Leuprolide Acetate), Lupron Depot (Leuprolide Acetate), Lupron Depot-Ped (Leuprolide Acetate), Lynparza (Olaparib), Marqibo (Vincristine Sulfate Liposome), Matulane (Procarbazine Hydrochloride), Mechlorethamine Hydrochloride, Megestrol Acetate, Mekinist (Trametinib), Melphalan, Melphalan Hydrochloride, Mercaptopurine, Mesna, Mesnex (Mesna), Methazolastone (Temozolomide), Methotrexate, Methotrexate LPF (Methotrexate), Methylnaltrexone Bromide, Mexate (Methotrexate), Mexate-AQ (Methotrexate), Midostaurin, Mitomycin C, Mitoxantrone Hydrochloride, Mitozytrex (Mitomycin C), MOPP, Mozobil (Plerixafor), Mustargen (Mechlorethamine Hydrochloride), Mutamycin (Mitomycin C), Myleran (Busulfan), Mylosar (Azacitidine), Mylotarg (Gemtuzumab Ozogamicin), Nanoparticle Paclitaxel (Paclitaxel Albumin-stabilized Nanoparticle Formulation), Navelbine (Vinorelbine Tartrate), Necitumumab, Nelarabine, Neosar (Cyclophosphamide), Neratinib Maleate, Nerlynx (Neratinib Maleate), Netupitant and Palonosetron Hydrochloride, Neulasta (Pegfilgrastim), Neupogen (Filgrastim), Nexavar (Sorafenib Tosylate), Nilandron (Nilutamide), Nilotinib, Nilutamide, Ninlaro (Ixazomib Citrate), Niraparib Tosylate Monohydrate, Nivolumab, Nolvadex (Tamoxifen Citrate), Nplate (Romiplostim), Obinutuzumab, Odomzo (Sonidegib), OEPA, Ofatumumab, OFF, Olaparib, Olaratumab, Omacetaxine Mepesuccinate, Oncaspar (Pegaspargase), Ondansetron Hydrochloride, Onivyde (Irinotecan Hydrochloride Liposome), Ontak (Denileukin Diftitox), Opdivo (Nivolumab), OPPA, Osimertinib, Oxaliplatin, Paclitaxel, Paclitaxel Albumin-stabilized Nanoparticle Formulation, PAD, Palbociclib, Palifermin, Palonosetron Hydrochloride, Palonosetron Hydrochloride and Netupitant, Pamidronate Disodium, Panitumumab, Panobinostat, Paraplat (Carboplatin), Paraplatin (Carboplatin), Pazopanib Hydrochloride, PCV, PEB, Pegaspargase, Pegfilgrastim, Peginterferon Alfa-2b, PEG-Intron (Peginterferon Alfa-2b), Pembrolizumab, Pemetrexed Disodium, Perjeta (Pertuzumab), Pertuzumab, Platinol (Cisplatin), Platinol-AQ (Cisplatin), Plerixafor, Pomalidomide, Pomalyst (Pomalidomide), Ponatinib Hydrochloride, Portrazza (Necitumumab), Pralatrexate, Prednisone, Procarbazine Hydrochloride, Proleukin (Aldesleukin), Prolia (Denosumab), Promacta (Eltrombopag Olamine), Propranolol Hydrochloride, Provenge (Sipuleucel-T), Purinethol (Mercaptopurine), Purixan (Mercaptopurine), Radium 223 Dichloride, Raloxifene Hydrochloride, Ramucirumab, Rasburicase, R-CHOP, R-CVP, Recombinant Human Papillomavirus (HPV) Bivalent Vaccine, Recombinant Human Papillomavirus (HPV) Nonavalent Vaccine, Recombinant Human Papillomavirus (HPV) Quadrivalent Vaccine, Recombinant Interferon Alfa-2b, Regorafenib, Relistor (Methylnaltrexone Bromide), R-EPOCH, Revlimid (Lenalidomide), Rheumatrex (Methotrexate), Ribociclib, R-ICE, Rituxan (Rituximab), Rituxan Hycela (Rituximab and Hyaluronidase Human), Rituximab, Rituximab and, Hyaluronidase Human, Rolapitant Hydrochloride, Romidepsin, Romiplostim, Rubidomycin (Daunorubicin Hydrochloride), Rubraca (Rucaparib Camsylate), Rucaparib Camsylate, Ruxolitinib Phosphate, Rydapt (Midostaurin), Sclerosol Intrapleural Aerosol (Talc), Siltuximab, Sipuleucel-T, Somatuline Depot (Lanreotide Acetate), Sonidegib, Sorafenib Tosylate, Sprycel (Dasatinib), STANFORD V, Sterile Talc Powder (Talc), Steritalc (Talc), Stivarga (Regorafenib), Sunitinib Malate, Sutent (Sunitinib Malate), Sylatron (Peginterferon Alfa-2b), Sylvant (Siltuximab), Synribo (Omacetaxine Mepesuccinate), Tabloid (Thioguanine), TAC, Tafinlar (Dabrafenib), Tagrisso (Osimertinib), Talc, Talimogene Laherparepvec, Tamoxifen Citrate, Tarabine PFS (Cytarabine), Tarceva (Erlotinib Hydrochloride), Targretin (Bexarotene), Tasigna (Nilotinib), Taxol (Paclitaxel), Taxotere (Docetaxel), Tecentriq, (Atezolizumab), Temodar (Temozolomide), Temozolomide, Temsirolimus, Thalidomide, Thalomid (Thalidomide), Thioguanine, Thiotepa, Tisagenlecleucel, Tolak (Fluorouracil—Topical), Topotecan Hydrochloride, Toremifene, Torisel (Temsirolimus), Tositumomab and Iodine I 131 Tositumomab, Totect (Dexrazoxane Hydrochloride), TPF, Trabectedin, Trametinib, Trastuzumab, Treanda (Bendamustine Hydrochloride), Trifluridine and Tipiracil Hydrochloride, Trisenox (Arsenic Trioxide), Tykerb (Lapatinib Ditosylate), Unituxin (Dinutuximab), Uridine Triacetate, VAC, Vandetanib, VAMP, Varubi (Rolapitant Hydrochloride), Vectibix (Panitumumab), VeIP, Velban (Vinblastine Sulfate), Velcade (Bortezomib), Velsar (Vinblastine Sulfate), Vemurafenib, Venclexta (Venetoclax), Venetoclax, Verzenio (Abemaciclib), Viadur (Leuprolide Acetate), Vidaza (Azacitidine), Vinblastine Sulfate, Vincasar PFS (Vincristine Sulfate), Vincristine Sulfate, Vincristine Sulfate Liposome, Vinorelbine Tartrate, VIP, Vismodegib, Vistogard (Uridine Triacetate), Voraxaze (Glucarpidase), Vorinostat, Votrient (Pazopanib Hydrochloride), Vyxeos (Daunorubicin Hydrochloride and Cytarabine Liposome), Wellcovorin (Leucovorin Calcium), Xalkori (Crizotinib), Xeloda (Capecitabine), XELIRI, XELOX, Xgeva (Denosumab), Xofigo (Radium 223 Dichloride), Xtandi (Enzalutamide), Yervoy (Ipilimumab), Yondelis (Trabectedin), Zaltrap (Ziv-Aflibercept), Zarxio (Filgrastim), Zejula (Niraparib Tosylate Monohydrate), Zelboraf (Vemurafenib), Zevalin (Ibritumomab Tiuxetan), Zinecard (Dexrazoxane Hydrochloride), Ziv-Aflibercept, Zofran (Ondansetron Hydrochloride), Zoladex (Goserelin Acetate), Zoledronic Acid, Zolinza (Vorinostat), Zometa (Zoledronic Acid), Zydelig (Idelalisib), Zykadia (Ceritinib), and/or Zytiga (Abiraterone Acetate).

E. EXAMPLES

66. The following examples are put forth so as to provide those of ordinary skill in the art with a complete disclosure and description of how the compounds, compositions, articles, devices and/or methods claimed herein are made and evaluated, and are intended to be purely exemplary and are not intended to limit the disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

1. Example 1

67. The NLRP3 inflammasome is a multi-protein complex that is dependent on the interaction between NLRP3 and the apoptosis-associated speck-like protein (ACS) to recruit caspase-1 for its role in sensing pathogenic microbes and activating IL-1β and IL-18 (FIG. 1). Homotypic interactions between the PYD domains of ASC and NLRP3 are critical for the formation of this complex (FIG. 2).

68. Using one of the α-helix of the NLRP3$^{PYD}$ (Shown in red in FIG. 2) as a template, a hydrocarbon-stapled α-helical peptide was developed to bind at the NLRP3 and ASC PYD:PYD interaction interface. As the PYD of NLRP3 exhibited poor biochemical behavior and was prone to aggregation, a fusion that incorporated a solubility-enhancing maltose-binding protein (MBP) was developed (FIG. 3). The NLRP3 PYD domain was expressed in *E. coli;* protein purification was carried out using Ni-NTA and size-exclusion chromatography. This construct yielded milligram quantities of protein after purification. Structural studies of the NLRP3-stapled peptide complex are being performed using x-ray crystallography (FIG. 4). POP1 is known to interact with ASCPYD to inhibit ASC oligomerization. Helix 2 of POP1 is a major component in this interaction and can be used as a template to evolve a higher affinity peptide ((FIG. 5). To generate additional peptide antagonists of NLRP3-ASC interactions, a yeast display can be used and directed evolution to select for high-affinity variants of a NLRP3-binding peptide derived from the protein POP1 (Table 3). Briefly, a mutated POP1 helix library fused to Aga2p can be expressed on the surface of yeast and combined with biotinylated NLRP3$^{PYD}$. A yeast display selection is performed by flow cytometric sorting (e.g., FACS or MACS). From this POP1 variants are obtained and then individual clones are screened and sequenced, and then stapled peptides are synthesized.

TABLE 3

| Helix 2 amino acid | Codon Type | Codon Variants | Amino Acid possibilities |
|---|---|---|---|
| E18 | VRG | 6 | E, G, K, Q, R (2) |
| K21 | MDG | 6 | K, L, M, Q, R (2) |
| K22 | MDG | 6 | K, L, M, Q, R (2) |
| M25 | NWS | 16 | D, E, F, H, I, K, M, N, Q, Y, V (2), L (3), stop |
| K26 | VDG | 9 | E, G, K, L, M, Q, V, R (2) |
| G28 | VWT | 6 | D, H, I, L, N, V |
| T29 | NDT | 12 | C, D, F, G, H, I, L, N, R, S, V, Y |
| V30 | VHT | 9 | A, D, H, I, L, N, P, T, V |

69. This construct yielded milligram quantities of protein after purification by Ni-NTA and size exclusion chromatography (FIGS. 6A and 6B). A helical stapled peptide was added to purified MBP-NLRP3 protein and subjected to sparse matrix crystallization screening. Several conditions were identified, and different crystal morphologies were observed (FIG. 7). The most prominent and reproducible crystals were spindle clusters and round needle clusters; optimization screens are ongoing. To evolve high-affinity POP1 peptides as inflammasome antagonists, a structure-guided mutant library was developed of POP1 residues at the NLRP3/ASC-binding site that includes >10$^7$ possible POP1 variants (FIG. 8). Co-crystallization studies of the inhibitor-MBP-NLRP3 complex revealed crystallization conditions that can be optimized to obtain a high-resolution structure.

F. REFERENCES

Mangan, M. S., et al. (2018). Targeting the NLRP3 inflammasome in inflammatory diseases. *Nature Reviews Drug Discovery,* 17 (8), 588-606

Oroz, J., et al. (2016). ASC Pyrin Domain Self-associates and Binds NLRP3 Protein Using Equivalent Binding Interfaces. J. Biol. Chem. 291: 19487-19501.

Liepinsh, E., et al. (2003). The death-domain fold of the ASC PYRIN domain, presenting a basis for PYRIN/PYRIN recognition. J. Mol. Biol. 332: 1155-1163.

Lu, A., & Wu, H. (2014). Structural mechanisms of inflammasome assembly. *FEBS Journal,* 282 (3), 435-444. doi:10.1111/febs.13133

G. SEQUENCE

SEQ ID NO: 1 amino acid sequence of POP1 Helix 2 sequence starting at residue 15 of POP1 LTPEELKKFKMKLGTVPLREG

What is claimed is:

1. An engineered inhibitor of NACHT, LRR and PYD domains-containing protein 3 (NLRP3) inflammasome, comprising a Helix 2 peptide of POP 1, wherein the Helix 2 peptide comprising one or more substitutions with different amino acid at residues E18, K21, K22, M25, K26, G28, T29, and/or V30 of POP1 as set forth in SEQ ID NO: 1, wherein the first residue of SEQ ID NO: 1 corresponds to residue L15 of POP1.

2. The engineered inhibitor of claim 1, wherein the amino acid at residue 18 comprises glycine, lysine, glutamine, or arginine.

3. The engineered inhibitor of claim 1, wherein the amino acid at residue 21 comprises leucine, methionine, glutamine, or arginine.

4. The engineered inhibitor of claim 1, wherein the amino acid at residue 22 comprises leucine, methionine, glutamine, or arginine.

5. The engineered inhibitor of claim 1, wherein the amino acid at residue 25 comprises aspartic acid, glutamic acid, phenylalanine, histidine, isoleucine, methionine, asparagine, glutamine, tyrosine, valine, or leucine.

6. The engineered inhibitor of claim 1, wherein the amino acid at residue 26 comprises glutamic acid, glycine, leucine, methionine, glutamine, valine, or arginine.

7. The engineered inhibitor of claim 1, wherein the amino acid at residue 28 comprises aspartic acid, histidine, isoleucine, leucine, asparagine, or valine.

8. The engineered inhibitor of of claim 1, wherein the amino acid at residue 29 comprises cysteine, aspartic acid, phenylalanine, glycine, histidine, isoleucine, leucine, asparagine, arginine, serine, valine, or tyrosine.

9. The engineered inhibitor of claim 1, wherein the amino acid at residue 30 comprises alanine, aspartic acid, histidine, isoleucine, leucine, asparagine, praline, threonine, or valine.

* * * * *